US008450697B2

(12) United States Patent
Ohtani

(10) Patent No.: US 8,450,697 B2
(45) Date of Patent: May 28, 2013

(54) DISCRIMINATION PARAMETER CALCULATION METHOD FOR PHOTON DETECTORS, AND NUCLEAR MEDICINE DIAGNOSTIC APPARATUS USING SAME

(75) Inventor: Atsushi Ohtani, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 883 days.

(21) Appl. No.: 12/597,814

(22) PCT Filed: Apr. 27, 2007

(86) PCT No.: PCT/JP2007/059179
§ 371 (c)(1),
(2), (4) Date: Oct. 27, 2009

(87) PCT Pub. No.: WO2008/139517
PCT Pub. Date: Nov. 20, 2008

(65) Prior Publication Data
US 2010/0133443 A1    Jun. 3, 2010

(51) Int. Cl.
*G01T 1/00* (2006.01)
*A61B 6/00* (2006.01)
(52) U.S. Cl.
USPC .......................................... 250/395; 250/583
(58) Field of Classification Search
USPC .................. 250/395, 367, 369, 370.08, 580, 250/81, 582, 583
See application file for complete search history.

(56) References Cited

U.S. PATENT DOCUMENTS 6,297,506 B1 * 10/2001 Young et al. ............... 250/369
2004/0178347 A1   9/2004 Murayama et al.
2006/0192128 A1   8/2006 Benlloch Bavciera et al.
2006/0261281 A1 * 11/2006 Tsuchiya et al. ......... 250/370.08
2009/0179154 A1   7/2009 Ooi

FOREIGN PATENT DOCUMENTS

| JP | 4-175684 A | 6/1992 |
| JP | 2000-56023 A | 2/2000 |
| JP | 2004-245592 A | 9/2004 |
| JP | 2004-279057 A | 10/2004 |
| JP | 2006-522925 A | 10/2006 |
| JP | 2007-93376 A | 4/2007 |
| JP | 2007-101191 A | 4/2007 |
| WO | WO-2007/043137 A1 | 4/2007 |

OTHER PUBLICATIONS

International Search Report for the Application No. PCT/JP2007/059179 mailed Aug. 7, 2007.

(Continued)

*Primary Examiner* — David Porta
*Assistant Examiner* — Faye Boosalis
(74) *Attorney, Agent, or Firm* — Cheng Law Group, PLLC

(57) ABSTRACT

A discrimination parameter calculation method for photon detectors in this invention, applies two types of fitting functions which approximate waveforms of count numbers relative to energy ratios to the data having accumulated output waveform signals, and calculates fitting parameters of both the fitting functions. Based on both the fitting parameters, count numbers which are 1/n of peaks of both the fitting functions, and a value of the energy ratio of both the fitting functions corresponding to the count numbers is calculated as discrimination parameter k. Thus, whatever kind first photon detecting elements 35 and second photon detecting elements 37 may be, since discrimination parameter k is automatically calculated based on the fitting parameters after carrying out a fitting with the fitting functions, the discrimination parameter can be calculated with high accuracy. It is therefore possible to obtain relatively easily discrimination parameter k which can fully bring out performance of the photon detectors 17.

15 Claims, 4 Drawing Sheets

OTHER PUBLICATIONS

Yoshida, Eiji "Dai 1-bu Jisedai PET Sochi Kaihatsu Kenkyu no Shinchoku Jokyo (6) Kenshutsuki Soshi Kosei", National Inst Radiol Sci, 2004, No. 172, pp. 51-55.

Yamamoto. S. et al., "A GSO Depth of Interaction Detector for PET", IEEE Transactions on Nuclear Science, 1998, vol. 45, No. 3, pp. 1078-1082.

MIT Virtual Museum PET text14, www.ricoh.co.jp/net-messensa/ACADEMIA/ JAMIT/ MITVM/PET/TANAKA04/text 14.html, Sep. 17, 2009.

Inadama, N., "A Measurement System of Depth of Interaction", Chiba University, www.nirs.go.jp/usr/medical-imaging/ja/study/nextgeneration-pet2000/ninadama.html, Sep. 17, 2009.

* cited by examiner

US 8,450,697 B2

DISCRIMINATION PARAMETER CALCULATION METHOD FOR PHOTON DETECTORS, AND NUCLEAR MEDICINE DIAGNOSTIC APPARATUS USING SAME

TECHNICAL FIELD

This invention relates to a discrimination parameter calculation method for photon detectors which detect photons such as X-rays and gamma rays, and a nuclear medicine diagnostic apparatus using the same, and more particularly to a technique for calculating a discrimination parameter used for determining depth information on photons undergoing interaction in the photon detectors, or also called DOI (Depth Of Interaction) detectors, having multiple layers of photon detecting elements of different types.

BACKGROUND ART

Conventional apparatus having DOI detectors include a DOI-PET (Positron Emission Tomography) apparatus, for example. In this apparatus, numerous DOI detectors first detect pair annihilation photons of 511 [keV] which are energy emitted from inside a patient administered with a positron-emitting radionuclide. When two DOI detectors detect photons within a definite period of time, they are counted as one pair of annihilation photons, and it is further determined that pair annihilation generating points exist on a straight line linking the DOI detector pair having detected them. RI (Radio Isotope) distribution images are created by accumulating such coincidence information and carrying out an image reconstruction process.

With the apparatus which calculates position information on the light source (=radiation source) from the position information on the DOI detectors and creates medical images from this information as noted above, the quality of medical images is improved by acquiring detailed position information on the DOI detectors. In detecting positions in a planar direction, for example, there is a technique of subdividing detectors or using a multi-anode type photomultiplier tube (PMT) (see Nonpatent Documents 1 and 2, for example). For detection in a depth direction, there is a technique of using DOI detectors having multiple layers of photon detecting elements of different types (see Nonpatent Document 3, and Patent Documents 1-3, for example).
[Nonpatent Document 1]
http://www.nirs.go.jp/use/medical-imaging/ja/study/next-generation-pet2000/ninadama.html
[Nonpatent Document 2]
http://www.ricoh.co.jp/net-messensa/ACADEMIA/JAMIT/MITVM/PET/TANAKA04/text14.html
[Nonpatent Document 3]
A GSO depth of interaction detector for PET: IEEE Trans. Nucl. Sci., 45: 1078-1082, 1998.
[Patent Document 1]
Unexamined Patent Publication No. 2000-56023
[Patent Document 2]
Unexamined Patent Publication No. 2004-245592
[Patent Document 3]
Patent National Publication No. 2006-522925

DISCLOSURE OF THE INVENTION

Problem to be Solved by the Invention

However, when a discrimination parameter is used for collected output waveform signals of DOI detectors to make a DOI determination, the accuracy of the discrimination parameter greatly influences the accuracy of depth information on the interaction.

Generally, an output waveform signal from each DOI detector contains numerous components such as components dependent on photon detecting elements constituting the DOI detector, noise components, and components generating from logic circuits, substrates and so on. When rates of interaction of radiation differ several or more times in the layers of photon detecting elements, the discrimination parameter may change or the calculation accuracy may lower, as outputs showing the waveforms of layers with low rates of interaction are entrained by outputs showing the waveforms of layers with high rates of interaction. Further, even with the same type of photon detecting elements, individual differences (individual characteristics) exist in their output waveform signals. It is therefore necessary to determine a discrimination parameter for each DOI detector, or periodical adjustment of the discrimination parameter is needed as a result of aging of the detector system.

Although the discrimination parameter is changeable with various factors as noted above, even when it is set to a value suitable to some extent, an improvement is found in position resolution concerning depth information of the interaction as compared with non-DOI detectors. However, there is a problem that this cannot fully bring out performance of the DOI detectors. A nuclear medicine diagnostic apparatus using such a discrimination parameter has a problem that high-quality RI distribution images cannot be obtained.

This invention has been made having regard to the state of the art noted above, and its object is to provide a discrimination parameter calculation method for photon detectors, and a nuclear medicine diagnostic apparatus using the same, which are capable of relatively easily obtaining a discrimination parameter which can fully bring out performance of the photon detectors.

Another object of this invention is to provide a nuclear medicine diagnostic apparatus which can obtain high-quality RI distribution images by using a discrimination parameter which can fully bring out performance of photon detectors.

Means for Solving the Problem

To fulfill the above object, this invention provides the following construction.

The invention set out in claim 1 provides a discrimination parameter calculation method for photon detectors, in which the photon detectors having multiple layers of photon detecting elements of different types located opposite a light source and in a back side, for calculating a discrimination parameter for carrying out pulse shape discrimination of output waveform signals, and determining photon detecting elements having carried out an interaction with photons, the discrimination parameter calculation method comprising a step of applying to data having accumulated the output waveform signals, two types of fitting functions which approximate waveforms of count numbers relative to energy ratios; a step of calculating fitting parameters of both the fitting functions; and a step of obtaining, based on both the fitting parameters, count numbers which are 1/n of peaks of both the fitting functions, and calculating a value of the energy ratio of both the fitting functions corresponding thereto as the discrimination parameter.

According to the invention set out in claim 1, two types of fitting functions which approximate waveforms of count numbers relative to energy ratios are first applied to the data having accumulated output waveform signals. Then, fitting parameters of both the fitting functions are calculated. Based on both the fitting parameters, count numbers which are 1/n of peaks of both the fitting functions are obtained, and a value of the energy ratio of both the fitting functions corresponding to the count numbers is calculated as discrimination parameter. That is, for probability distributions of photons detected by the respective photon detecting elements, a value of the energy ratio of both the fitting functions corresponding to the count numbers which will remove 1/n from both the probability distributions is obtained as discrimination parameter. Thus, whatever kind the photon detecting elements may be, since a discrimination parameter is automatically calculated based on the fitting parameters after carrying out a fitting with the fitting functions, the discrimination parameter can be calculated with high accuracy. It is therefore possible to obtain relatively easily a discrimination parameter which can fully bring out performance of the photon detectors.

In this invention, it is preferred that, when a sum total value of count numbers at peaks of both the fitting functions is less than a predetermined value, a lower limit or an upper limit of the energy ratio is set as the discrimination parameter (claim 2).

According to the invention set out in claim 2, when the count numbers are less than the predetermined value, a discrimination parameter cannot be obtained with high accuracy, and therefore, by setting a lower limit or an upper limit of the energy ratio as the discrimination parameter, it can be distinguished easily from a discrimination parameter calculated with high accuracy.

The energy ratio is energy detected by the photon detectors within a certain time, divided by entire energy. In terms of hardware, it takes a value between a certain upper limit and a certain lower limit. Thus, since the discrimination parameter usually is not an upper limit or a lower limit, it can be distinguished from a discrimination parameter calculated normally.

In this invention, it is preferable to further provide a step of determining propriety of both the fitting parameters, after the fitting parameters are calculated, based on whether both the fitting parameters are within a predetermined range derived beforehand from experimental values, wherein, when one of the fitting parameters is determined improper, a lower limit or an upper limit of the energy ratio is set as the discrimination parameter (claim 3).

According to the invention set out in claim 3, experiments are conducted beforehand on the fitting parameters to check what ranges the fitting parameters fall in. When they are outside the ranges, it is highly possible that a certain problem has arisen, such as a failure in calculation of the fitting parameters or a problem with the photon detectors per se. Then, when the fitting parameters are determined unsuitable, it is impossible to obtain a discrimination parameter with high accuracy based on the fitting parameters. By setting a lower limit or an upper limit which is usually impossible, it can be distinguished easily from a discrimination parameter obtained normally.

In this invention, it is preferred that the step of applying the fitting functions carries out a fitting, using one of the peaks as reference, only within a predetermined range derived beforehand from experimental values and including the reference (claim 4).

According to the invention set out in claim 4, the discrimination parameter can be calculated as long as at least data between the peaks of the two fitting functions is available. Thus, experiments are conducted to set an approximate position of one of the peaks and a range including the vicinity of the other peak. Then, a fitting is not carried out outside that range, whereby the load of the process for calculating the discrimination parameter can be lightened, and the time taken by the calculation process can be shortened.

In this invention, it is preferable to further provide a step of determining propriety of the discrimination parameter, after the discrimination parameter is calculated, based on whether the discrimination parameter is between energy ratios corresponding to the peaks of both the fitting functions (claim 5).

According to the invention set out in claim 5, after the discrimination parameter is calculated, propriety of the discrimination parameter is determined based on whether the discrimination parameter is between energy ratios corresponding to the peaks of both the fitting functions. Thus, propriety of the discrimination parameter can be determined easily.

In this invention, it is preferred that, when the discrimination parameter is determined improper, an upper limit or a lower limit of the energy ratio is set as the discrimination parameter (claim 6).

According to the invention set out in claim 6, when the discrimination parameter is improper, an upper limit or a lower limit is set as its value, thereby rendering it easily distinguishable from a discrimination parameter obtained normally.

In this invention, it is preferable to provide a step of displaying on a crystal display portion, after the discrimination parameter is calculated, discrimination parameters and fitting functions of all blocks of a plurality of individual blocks formed by dividing the photon detecting elements; a step of selecting an arbitrary block on the crystal display portion as a particular block; a step of displaying the fitting functions and the discrimination parameter of the particular block on an adjustment display portion; and a step of displaying a composite function which is a sum of the fitting functions of all the blocks and the discrimination parameter of the particular block on a block display portion; and further comprise a step executed, when the discrimination parameter of the particular block is arbitrarily adjusted after all the steps, to display the discrimination parameter adjusted on the adjustment display portion and the block display portion, and fine-adjust the discrimination parameter of the particular block (claim 7).

According to the invention set out in claim 7, after the discrimination parameter is calculated, discrimination parameters and fitting functions of all blocks of a plurality of individual blocks formed by dividing the photon detecting elements are displayed on the crystal display portion. Further, an arbitrary block on the crystal display portion is selected as a particular block, and the fitting functions and the discrimination parameter of the particular block are displayed on the adjustment display portion. Then, a composite function which is a sum of the fitting functions of all the blocks and the discrimination parameter of the particular block are displayed on the block display portion. Subsequently, when the discrimination parameter of the particular block is arbitrarily adjusted, the discrimination parameter adjusted is displayed on the adjustment display portion and the block display portion, to allow the discrimination parameter of the particular block to be fine-adjusted visually and easily.

The invention set out in claim 8 provides a nuclear medicine diagnostic apparatus for detecting photons from a patient, comprising a bed for supporting the patient; photon detectors having multiple layers of photon detecting elements of different types located opposite the bed and in a back side, for detecting photons emitted from a radionuclide injected into the patient; a discrimination parameter calculating device for applying to data having accumulated the output waveform signals, two types of fitting functions which approximate waveforms of count numbers relative to energy ratios, calculating fitting parameters of both the fitting functions, obtaining, based on both the fitting parameters, count numbers which are 1/n of peaks of both the fitting functions, and calculating a value of the energy ratio of both the fitting functions corresponding thereto as the discrimination parameter; and a reconstructing device for reconstructing RI distribution images based on the data and the discrimination parameter.

According to the invention set out in claim 8, the photons emitted from the patient placed on the bed are detected by the multilayer photon detectors. The discrimination parameter therefor is obtained as follows.

Two types of fitting functions which approximate waveforms of count numbers relative to energy ratios are first applied to the data having accumulated output waveform signals. Fitting parameters of both the fitting functions are calculated. Based on both the fitting parameters, count numbers which are 1/n of peaks of both the fitting functions are obtained, and a value of the energy ratio of both the fitting functions corresponding to the count numbers is calculated as discrimination parameter. In other words, for probability distributions of photons detected by the respective photon detecting elements, a value of the energy ratio of both the fitting functions corresponding to the count numbers which will remove 1/n from both the probability distributions is obtained as discrimination parameter. Thus, whatever kind the photon detecting elements may be, since a discrimination parameter is automatically calculated based on the fitting parameters after carrying out a fitting with the fitting functions, the discrimination parameter can be calculated with high accuracy. It is therefore possible to obtain relatively easily a discrimination parameter which can fully bring out performance of the photon detectors. Since the reconstructing device reconstructs RI distribution images based on the highly accurate discrimination parameter obtained in this way and the data, high-quality RI distribution images using high-precision depth position information can be acquired.

Effects of the Invention

According to the discrimination parameter calculation method for photon detectors of this invention, two types of fitting functions which approximate waveforms of count numbers relative to energy ratios are first applied to the data having accumulated output waveform signals. Then, fitting parameters of both the fitting functions are calculated. Based on both the fitting parameters, count numbers which are 1/n of peaks of both the fitting functions are obtained, and a value of the energy ratio of both the fitting functions corresponding to the count numbers is calculated as discrimination parameter. That is, for probability distributions of photons detected by the respective photon detecting elements, a value of the energy ratio of both the fitting functions corresponding to the count numbers which will remove 1/n from both the probability distributions is obtained as discrimination parameter. Thus, whatever kind the photon detecting elements may be, since a discrimination parameter is automatically calculated based on the fitting parameters after carrying out a fitting with the fitting functions, the discrimination parameter can be calculated with high accuracy. It is therefore possible to obtain relatively easily a discrimination parameter which can fully bring out performance of the photon detectors.

DESCRIPTION OF REFERENCES

Figure 1:
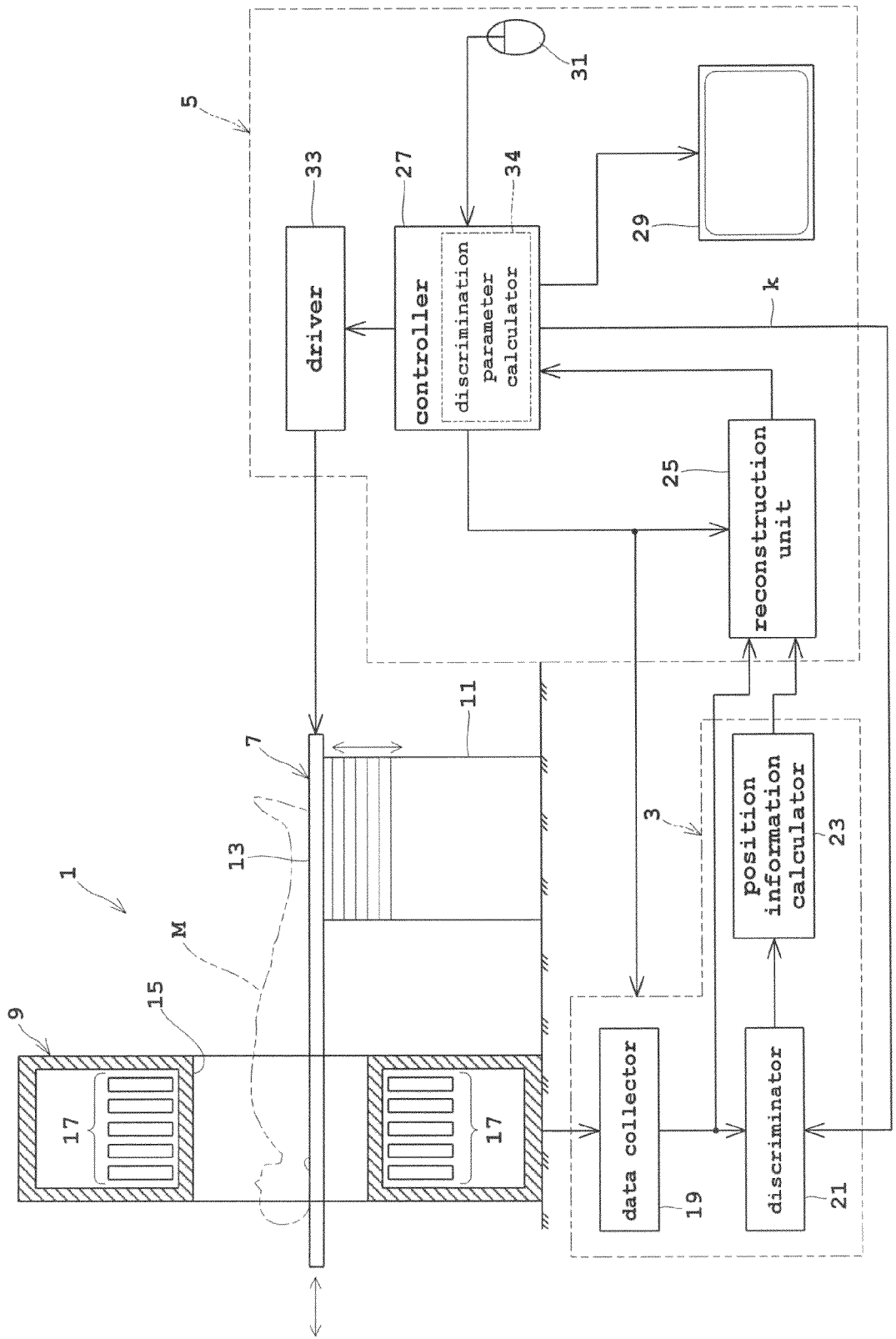
FIG. 1 is a block diagram showing an outline of a positron CT apparatus according to an embodiment.

M . . . patient
1 . . . gantry unit
3 . . . data collecting system
5 . . . data processor
7 . . . bed
9 . . . gantry
17 . . . photon detectors
19 . . . data collector
21 . . . discriminator
23 . . . position information calculator
25 . . . reconstruction unit
27 . . . controller
29 . . . display unit
31 . . . instruction unit
34 . . . discrimination parameter calculator
35 . . . first photon detecting elements
37 . . . second photon detecting elements
41 . . . photomultiplier tubes
k . . . discrimination parameter

BEST MODE FOR CARRYING OUT THE INVENTION

For probability distributions of photons detected by respective photon detecting elements, a value of energy ratio of both fitting functions which remove 1/n from both the probability distributions and correspond to count numbers is obtained as discrimination parameter. Thus, whatever kind the photon detecting elements may be, since the discrimination parameter is automatically calculated based on the fitting parameters after carrying out a fitting with the fitting functions, the discrimination parameter can be calculated with high accuracy. This fulfills the object of being capable of relatively easily obtaining a discrimination parameter which can fully bring out performance of the photon detectors.

Embodiment 1

Figure 2:
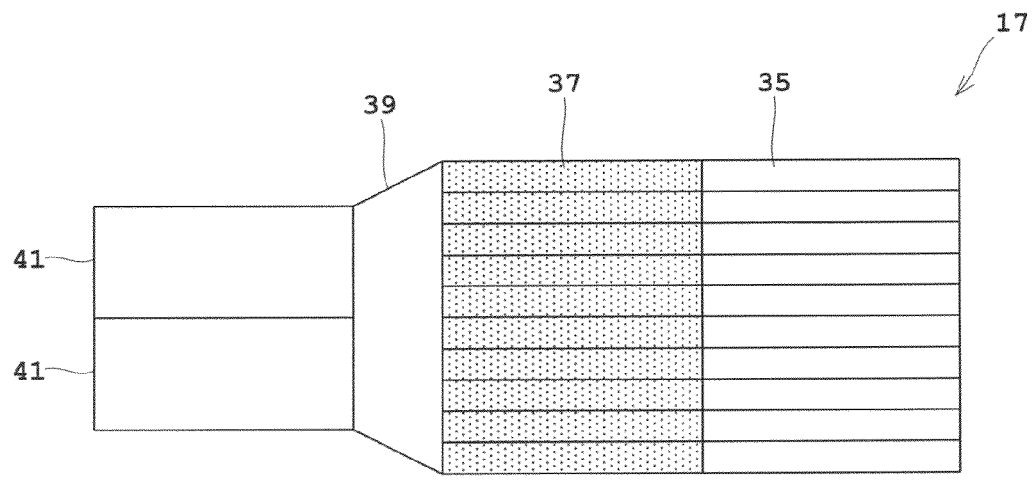
FIG. 2 is a view in vertical section showing an outline of a photon detector.

Embodiment 1 of this invention will be described hereinafter with reference to the drawings. FIG. 1 is a block diagram showing an outline of a positron CT apparatus according to the embodiment. FIG. 2 is a view in vertical section showing an outline of a photon detector.

This positron CT apparatus includes a gantry unit 1, a data collecting system 3 and a data processor 5. The gantry unit 1 includes a bed 7 for supporting a patient M medicated with a positron-emitting radionuclide, and a gantry 9. The bed 7 includes a vertically movable base block 11, and a top board 13 horizontally movable on the base block 11.

The gantry 9 has an opening 15 formed centrally thereof for receiving the patient M along with the top board 13. A plurality of photon detectors 17 (described in detail hereinafter) are embedded around the opening 15 for detecting positrons (photons) released from the patient M. Outputs from the plurality of photon detectors 17 are given to the data collecting system 3.

The data collecting system 3 includes a data collector 19, a discriminator 21 and a position information calculator 23. The data collector 19 has an amplifier, an ADC (analog-digital converter), a TDC (time-digital converter), a delay circuit and a double event determiner, for collecting and digitizing signals relating to photons coincident on a pair of photon detectors 17. The discriminator 21, based on a discrimination parameter set beforehand (described in detail hereinafter), carries out pulse shape discrimination of data of output waveform signals outputted from the photon detectors 17 and collected by the data collector 19, and determines photon detecting elements in the photon detectors 17 having interacted with photons, as described hereinafter. The position information calculator 23, based on the data of the output waveform signals and depth information (z) of interaction, obtains position information (x, y, z) on the interaction of photons.

The data processor 5 includes a reconstruction unit 25, a controller 27, a display unit 29, an instruction unit 31 and a driver 33. The reconstruction unit 25 reconstructs RI distribution images of the patient M based on the position information from the position information calculator 23, the data of the output waveform signals from the data collector 19 and transmission data collected separately. The controller 27 has a discrimination parameter calculator 34, and carries out an automatic calculation process for a discrimination parameter described hereinafter, an automatic determination process for automatically determining propriety of the discrimination parameter obtained, a fine adjustment process for fine-adjusting the discrimination parameter, a process of causing the display unit 29 to display RI distribution images based on the data of the reconstruction unit 25, a process of driving the top board 13 back and forth through the driver 33 based on instructions given through the instruction unit 31 such as a mouse, and instructions for the data collecting system 3 to start collection.

The above reconstruction unit 25 corresponds to the reconstructing device in this invention. The above discrimination parameter calculator 34 corresponds to the discrimination parameter calculating device in this invention.

The photon detectors 17 are constructed as shown in FIG. 2, for example.

That is, the photon detectors 17 are what are called two-layer DOI detectors constructed by combining a plurality of photon detecting elements of different types, and then laminating them. Specifically, first photon detecting elements 35 and second photon detecting elements 37 are arranged in order from a photon-emitting direction (from the bed 7). A light guide 39 is disposed adjacent the second photon detecting elements 37, and further a plurality of photomultiplier tubes 41 are arranged on the light guide 39. The photomultiplier tubes 41, preferably, are what are called the mono-anode type. In the first photon detecting elements 35 and second photon detecting elements 37, each detecting element comprises a plurality of blocks. The first photon detecting elements 35 are formed of LSO (lutium silicon oxide), for example. The second photon detecting elements 37 are formed of GSO (gadolinium silicon oxide), for example.

Figure 3:
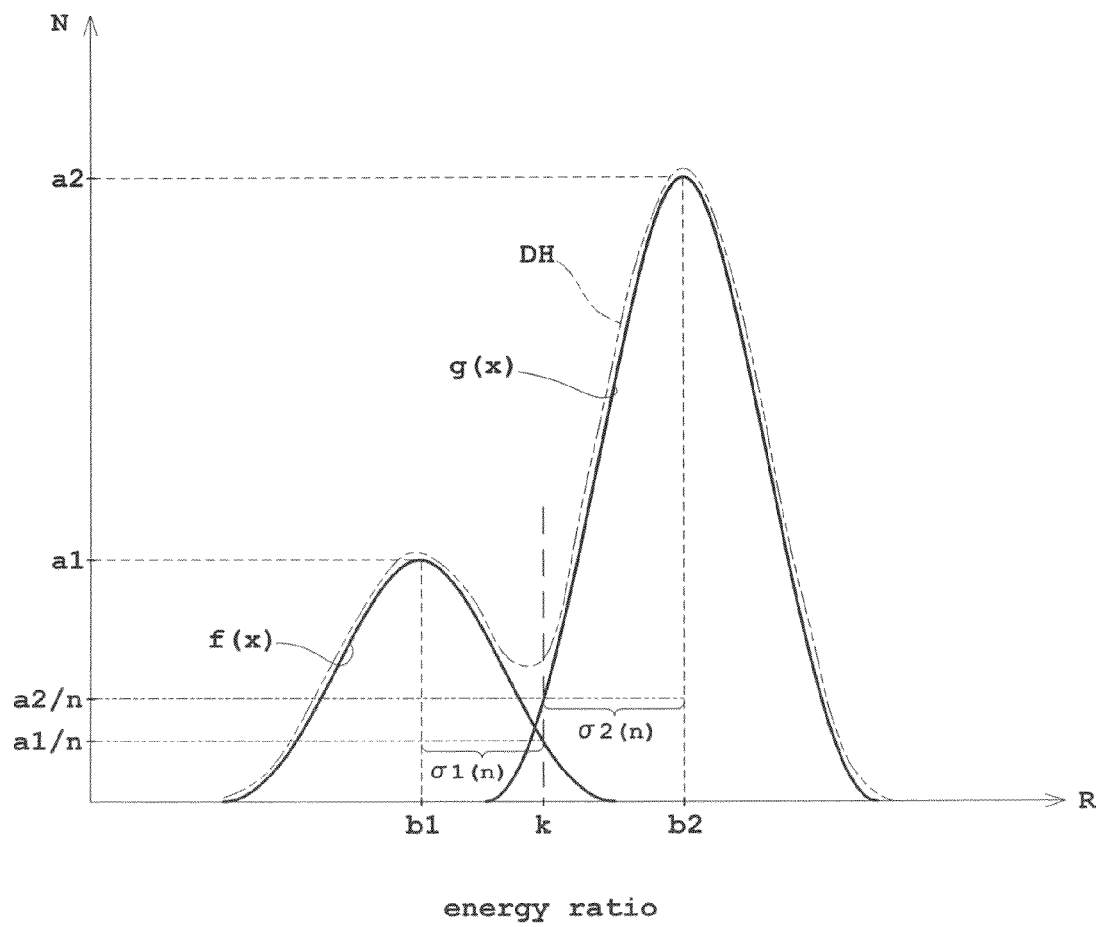
FIG. 3 is a graph showing an example of histogram of count numbers relative to energy ratios.

Reference is now made to FIG. 3. FIG. 3 is a graph showing an example of histogram of count numbers relative to energy ratios. An energy ratio is energy detected by the photon detectors 17 within a certain time, divided by entire energy. In terms of hardware, it takes a value between a certain upper limit (e.g. 256) and a certain lower limit (e.g. 1).

The data of the output waveform signals from the photon detectors 17 includes numerous components such as outputs dependent on the detecting elements and outputs due to noise components. Here, in the histogram accumulating outputs representing waveforms thereof, each component shall take a Gaussian distribution (normal distribution). In the above histogram (e.g. consisting of two components), it is well known that, when fitting functions having two Gaussian distributions are used, the histogram can be expressed well with the fitting functions.

A method of calculating the discrimination parameter after carrying out a fitting as noted above will be described hereinafter. Here, in order to facilitate understanding of the description, the two-layer DOI detectors (photon detectors 17) shown in FIG. 2 will be described by way of example.

In this case, histogram DH of the data having accumulated the output waveform signals presents a Gaussian distribution based on components of the first detecting elements 35 and a Gaussian distribution based on components of the second detecting elements 37. So, in the following description, discrimination parameter k is calculated using the two Gaussian distributions. The basic concept of the method of calculating discrimination parameter k described hereinafter is that the portion where the two Gaussian distributions are both 1/n (n takes a real number) is regarded as discrimination parameter k.

Here, two Gaussian functions are defined as fitting functions as follows. Signs a1, a2, b1, b2, c1 and c2 represent fitting parameters in the fitting functions.

$$f(x) = a1 \times \exp\{-(x-b1)^2/c1^2\}$$

$$g(x) = a2 \times \exp\{-(x-b2)^2/c2^2\}$$

At this time, the 1/n widths of both Gaussian functions are given by the following equations:

$$\sigma1(n) = c1 \times \sqrt{(\ln n)}$$

$$\sigma2(n) = c2 \times \sqrt{(\ln n)}$$

When the 1/n widths of these peaks are used, discrimination parameter k is expressed as follows:

$$k = b1 + \sigma1(n)$$

$$k = b2 - \sigma2(n)$$

The above equations are solved to give $$k = (c2 \times b1 + c1 \times b2)/(c1+c2).$$

It will be understood that, as noted above, discrimination parameter k can be derived easily from fitting parameters a1, a2, b1, b2, c1 and c2 of the fitting functions.

Next, an automatic calculation method and an automatic determination method will be described.

What is required for automatic calculation of discrimination parameter k is to determine automatically initial fitting parameters appropriate for carrying out the fitting. A histogram accumulating outputs representing waveforms differs for each of the first photon detecting elements 35 and second photon detecting elements 37 of the photon detectors 17, but generally the tendency is the same. Thus, fitting parameters are determined with reference to a certain portion.

Take FIG. 3 for example, fitting parameters a2 and b2 of Gaussian function g(x) are a maximum count value (peak) and each output value (energy ratio) corresponding thereto, in the histogram of count numbers relative to energy ratios, and can therefore be searched easily. Thus, based on fitting parameters a2 and b2 of one Gaussian function g(x), fitting parameters a1 and b1 of the other Gaussian function f(x) are derived from the following equations:

$$a1 = a2 \times 0.6$$

$$b1 = b2 - 30$$

The above constants 0.6 and 30 have been determined by conducting experiments beforehand with actual equipment.

Incidentally, it is preferred that the range for carrying out the fitting is limited to an area required to carry out the fitting. Thus, from the fitting parameters obtained, the fitting is carried out only for a proper range. Specifically, in the histogram shown in FIG. 3, with reference to the position of fitting parameter b2, the fitting is carried out only within a predetermined range derived beforehand from experimental values, and including the reference. For example, it is a range of −90 to 40 with reference to fitting parameter b2. By limiting the range for carrying out the fitting in this way, the load of the process for calculating the discrimination parameter can be lightened, and the time taken by the calculation process can be shortened.

When the total value of count numbers (a1+a2) at the peaks of the fitting functions is less than a predetermined value, it is preferable to set a lower limit or upper limit of the energy ratio as discrimination parameter. When the count numbers are less than the predetermined value, a discrimination parameter cannot be obtained with high accuracy. Thus, by setting a lower limit or upper limit of the energy ratio as discrimination parameter, it can be distinguished easily from a discrimination parameter calculated with high accuracy.

Next, when the above condition is fulfilled, determination is automatically made as to propriety of discrimination parameter k calculated automatically.

That is, since discrimination parameter k is present between the peaks of fitting functions f(x) and g(x), discrimination parameter k should fulfill the following condition:

$$b1 \leq k \leq b2$$

The above condition is not fulfilled, an upper limit, for example, is set to discrimination parameter k calculated automatically. That is, k=256.

Experiments may be conducted with actual equipment beforehand on the fitting parameters a1, a2, b1, b2, c1 and c2, to check what ranges of values are taken by the fitting parameters a1, a2, b1, b2, c1 and c2, and propriety of discrimination parameter k may be determined strictly by whether the fitting parameters a1, a2, b1, b2, c1 and c2 are within these ranges, respectively. The above ranges are 140<b1<160 and 160<b2<200, for example.

When the fitting parameters are outside the ranges, it is highly possible that a certain problem has arisen, such as a failure in calculation of the fitting parameters or a problem with the photon detectors 17 per se. Then, when the fitting parameters are determined unsuitable, it is impossible to obtain discrimination parameter k with high accuracy based on the fitting parameters. By setting an upper limit (e.g. k=356) or lower limit (e.g. k=1) which is usually impossible, it can be distinguished easily from discrimination parameter k obtained normally.

Discrimination parameter k calculated by the discrimination parameter calculator 34 of the controller 27 with its propriety determined as described above is stored in a data file for each detector block. When the data file is opened and a detector block is designated, the discrimination parameter k is displayed on the display unit 29.

Figure 4:
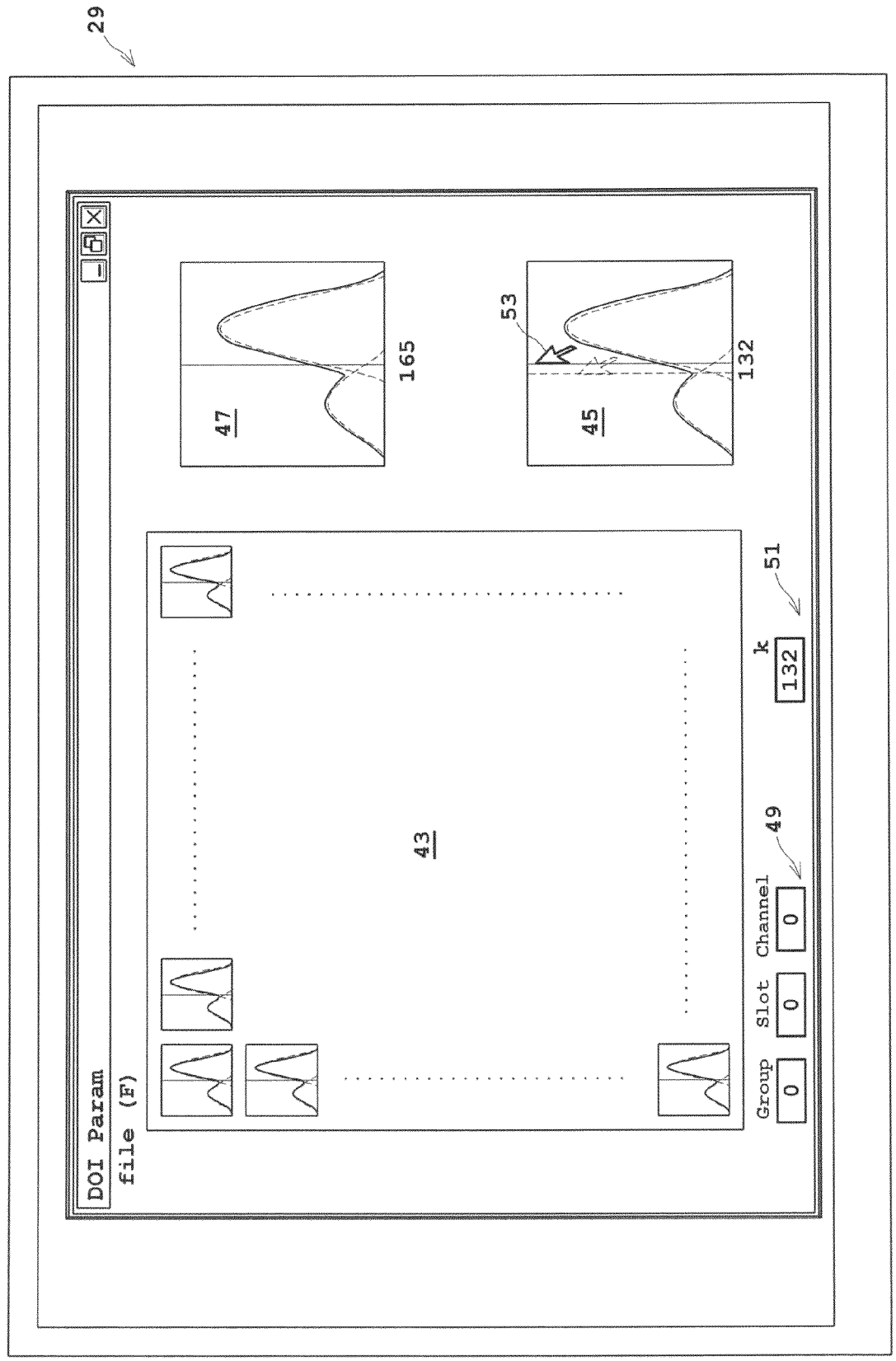
FIG. 4 is a view showing an example of display on a display unit.

Reference is now made to FIG. 4. FIG. 4 is a view showing an example of display on the display unit.

This display unit 29 has three display areas set thereto as main areas.

That is, a crystal display portion 43, an adjustment display portion 45 and a block display portion 47 are provided. Below the crystal display portion 43 are a designation area 49 for designating the detector blocks, and a discrimination parameter input portion 51.

The crystal display portion 43 is an area for displaying discrimination parameters k and fitting functions of all blocks, with respect to a plurality of individual blocks provided by dividing the first photon detecting elements 35 and second photon detecting elements 37 of the photon detectors 17. Discrimination parameter k determined to be unsuitable as noted above, preferably, is displayed conspicuously to indicate that it is determined unsuitable, by displaying it in a red frame or by blinking the display.

The adjustment display portion 45 is an area for displaying the fitting functions and discrimination parameter of a particular block instructed by the instruction unit 31, among arbitrary blocks on the crystal display portion 43.

The block display portion 47 is an area for displaying a composite function which is a total of the fitting functions of all the blocks displayed on the crystal display portion 43, and the discrimination parameter of the particular block.

For example, the instruction unit 31 selects a desired block from among the blocks displayed on the crystal display portion 43, and the fitting functions and discrimination parameter of the particular block are displayed on the adjustment display portion 45. Looking at the display, the operator determines propriety of discrimination parameter k obtained through the automatic calculation. When it is determined that adjustment is required, the instruction unit 31 is operated for causing a cursor 53 to drag the discrimination parameter k displayed on the adjustment display portion 45, to make fine adjustment to a desired value. Alternatively, the discrimination parameter k is fine-adjusted by directly inputting a numerical value to the discrimination parameter input portion 51.

The above instruction unit 31 corresponds to the selecting device and adjusting device in this invention.

The calculation and propriety determination are carried out automatically as described above, and subsequently the fine-adjusted discrimination parameter k is saved on instructions from the instruction unit 31, and is set as discrimination parameter k for the discriminator 21.

According to the discrimination parameter calculation method for the photon detectors 17 in this embodiment, as described above, two types of fitting functions which approximate waveforms of count numbers relative to energy ratios are first applied to the data having accumulated output waveform signals. Then, fitting parameters of both the fitting functions are calculated. Based on both the fitting parameters, count numbers which are 1/n of peaks of both the fitting functions, and a value of the energy ratio of both the fitting functions corresponding to the count numbers is calculated as discrimination parameter k. That is, for probability distributions of photons detected by the first photon detecting elements 35 and second photon detecting elements 37, a value of the energy ratio of both the fitting functions corresponding to the count numbers which will remove 1/n from both the probability distributions is obtained as discrimination parameter. Thus, whatever kind the first photon detecting elements 35 and second photon detecting elements 37 may be, since discrimination parameter k is automatically calculated based on the fitting parameters after carrying out a fitting with the fitting functions, the discrimination parameter can be calculated with high accuracy. It is therefore possible to obtain relatively easily discrimination parameter k which can fully bring out performance of the photon detectors 17.

Figure 5:
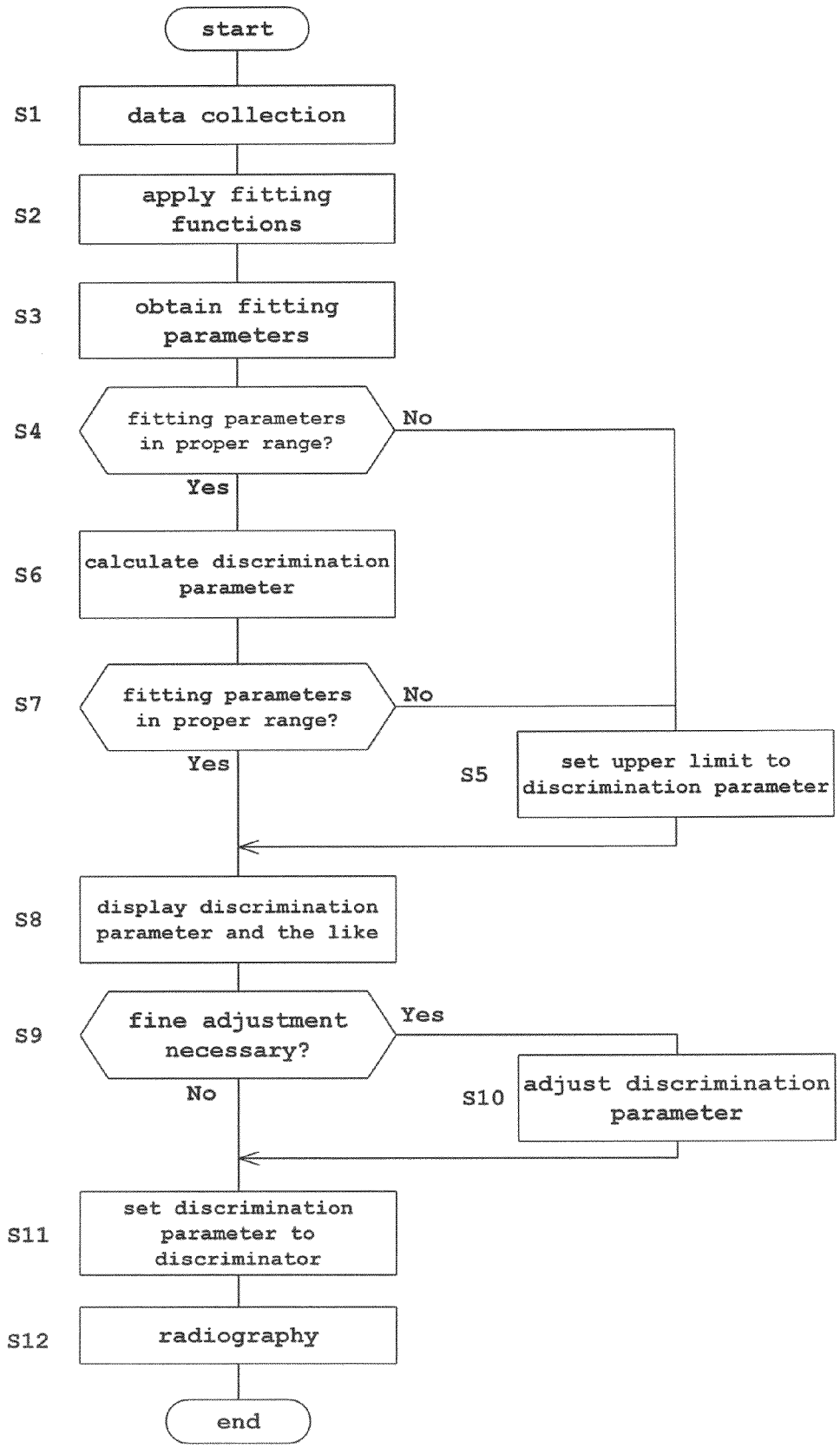
FIG. 5 is a flow chart showing an example of operation.

Next, operation of the positron CT apparatus of having the above construction will be described with reference to FIG. 5. FIG. 5 is a flow chart showing an example of operation.

Step S1

The controller 27 operates various components to cause a predetermined radiation source to emit radiation, and to cause the data collector 19 to collect data in this state.

Steps S2 and S3

The discrimination parameter calculator 34 of the controller 27 applies the fitting functions, by the foregoing calculation method, to obtain fitting parameters automatically.

Steps S4-S8

Propriety of the fitting parameters is determined. When they are found proper, discrimination parameter k is calculated. When found improper, an upper limit is set to discrimination parameter k. Then, the discrimination parameter k and the like are displayed on the display unit 29.

Steps S9-S11

The discrimination parameter k and the like displayed on the display unit 29 are observed, and if fine adjustment is required, fine adjustment is carried out. And finally the discrimination parameter k is set to the discriminator 21.

Step S12

Radiography is carried out with the patient M placed on the bed 7. Depth information (z) is obtained by carrying out pulse shape discrimination of collected data with the discrimination parameter k, and the reconstruction unit 25 reconstructs RI distribution images based on positional information on the collected data (x, y). The RI distribution images are displayed on the display unit 29.

Thus, according to the apparatus in this embodiment using the foregoing discrimination parameter calculation method, since the discrimination parameter calculator 34 automatically calculates the discrimination parameter k based on the fitting parameters after carrying out a fitting with the fitting functions, the discrimination parameter k can be calculated with high accuracy. It is therefore possible to obtain relatively easily discrimination parameter k which can fully bring out performance of the photon detectors 17. Since the reconstruction unit 25 reconstructs RI distribution images based on the highly accurate discrimination parameter obtained in this way and the data, high-quality RI distribution images using high-precision depth position information can be acquired.

This invention is not limited to the foregoing embodiment, but may be modified as follows:

(1) In the foregoing embodiment, Gaussian functions are used as fitting functions when obtaining discrimination parameter k, but other functions may be used. For example, linear functions may be used to offsets of noise.

(2) In the foregoing embodiment, an upper limit or lower limit is set for an improper discrimination parameter. For example, a different specific value may be set instead.

(3) In the foregoing embodiment, a fitting is carried out only in a specific range. A fitting may be carried over the entire range.

(4) In the foregoing embodiment, one photon detector 17 is the mono-anode type, but instead may be the multi-anode type, for example. This can lessen the photomultiplier tubes 41 to reduce cost.

(5) The foregoing embodiment has been described taking the positron CT apparatus for example. It is applicable also to a nuclear medicine diagnostic apparatus using a single photon emitting nuclide (SPECT apparatus).

INDUSTRIAL UTILITY

As described above, this invention is suitable for an apparatus which carries out nuclear medicine diagnosis for creating RI distribution images based on depth information on photon interactions.

The invention claimed is:

1. A discrimination parameter calculation method for photon detectors, in which the photon detectors having multiple layers of photon detecting elements of different types located opposite a light source and in a back side, for calculating a discrimination parameter for carrying out pulse shape discrimination of output waveform signals, and determining photon detecting elements having carried out an interaction with photons, the discrimination parameter calculation method comprising a step of applying to data having accumulated the output waveform signals, two types of fitting functions which approximate waveforms of count numbers relative to energy ratios; a step of calculating fitting parameters of both the fitting functions; and a step of obtaining, based on both the fitting parameters, count numbers which are 1/n of peaks of both the fitting functions, and calculating a value of the energy ratio of both the fitting functions corresponding thereto as the discrimination parameter.

2. The discrimination parameter calculation method for photon detectors according to claim 1, wherein, when a sum total value of count numbers at peaks of both the fitting functions is less than a predetermined value, a lower limit or an upper limit of the energy ratio is set as the discrimination parameter.

3. The discrimination parameter calculation method for photon detectors according to claim 2, further comprising a step of determining propriety of both the fitting parameters, after the fitting parameters are calculated, based on whether both the fitting parameters are within a predetermined range derived beforehand from experimental values, wherein, when one of the fitting parameters is determined improper, a lower limit or an upper limit of the energy ratio is set as the discrimination parameter.

4. The discrimination parameter calculation method for photon detectors according to claim 1, further comprising a step of determining propriety of both the fitting parameters, after the fitting parameters are calculated, based on whether both the fitting parameters are within a predetermined range derived beforehand from experimental values, wherein, when one of the fitting parameters is determined improper, a lower limit or an upper limit of the energy ratio is set as the discrimination parameter.

5. The discrimination parameter calculation method for photon detectors according to claim 1, wherein the step of applying the fitting functions carries out a fitting, using one of the peaks as reference, only within a predetermined range derived beforehand from experimental values and including the reference.

6. The discrimination parameter calculation method for photon detectors according to claim 1, further comprising a step of determining propriety of the discrimination parameter, after the discrimination parameter is calculated, based on whether the discrimination parameter is between energy ratios corresponding to the peaks of both the fitting functions.

7. The discrimination parameter calculation method for photon detectors according to claim 6, wherein, when the discrimination parameter is determined improper, an upper limit or a lower limit of the energy ratio is set as the discrimination parameter.

8. The discrimination parameter calculation method for photon detectors according to claim 1, comprising a step of displaying on a crystal display portion, after the discrimination parameter is calculated, discrimination parameters and fitting functions of all blocks of a plurality of individual blocks formed by dividing the photon detecting elements; a step of selecting an arbitrary block on the crystal display portion as a particular block; a step of displaying the fitting functions and the discrimination parameter of the particular block on an adjustment display portion; and a step of displaying a composite function which is a sum of the fitting functions of all the blocks and the discrimination parameter of the particular block on a block display portion; and further comprising a step executed, when the discrimination parameter of the particular block is arbitrarily adjusted after all the steps, to display the discrimination parameter adjusted on the adjustment display portion and the block display portion, and fine-adjust the discrimination parameter of the particular block.

9. A nuclear medicine diagnostic apparatus for detecting photons from a patient, comprising a bed for supporting the patient; photon detectors having multiple layers of photon detecting elements of different types located opposite the bed and in a back side, for detecting photons emitted from a radionuclide injected into the patient; a discrimination parameter calculating device for applying to data having accumulated the output waveform signals, two types of fitting functions which approximate waveforms of count numbers relative to energy ratios, calculating fitting parameters of both the fitting functions, obtaining, based on both the fitting parameters, count numbers which are 1/n of peaks of both the fitting functions, and calculating a value of the energy ratio of both the fitting functions corresponding thereto as the discrimination parameter; and a reconstructing device for reconstructing RI distribution images based on the data and the discrimination parameter.

10. The nuclear medicine diagnostic apparatus according to claim 9, wherein the parameter calculating device sets, when a sum total value of count numbers at peaks of both the fitting functions is less than a predetermined value, a lower limit or an upper limit of the energy ratio is set as the discrimination parameter.

11. The nuclear medicine diagnostic apparatus according to claim 10, wherein the parameter calculating device determines propriety of both the fitting parameters, after the fitting parameters are calculated, based on whether both the fitting parameters are within a predetermined range derived beforehand from experimental values, and, when one of the fitting parameters is determined improper, sets a lower limit or an upper limit of the energy ratio as the discrimination parameter.

12. The nuclear medicine diagnostic apparatus according to claim 10, wherein the parameter calculating device, when applying the fitting functions, carries out a fitting, using one of the peaks as reference, only within a predetermined range derived beforehand from experimental values and including the reference.

13. The nuclear medicine diagnostic apparatus according to claim 10, wherein the parameter calculating device determines propriety of the discrimination parameter, after the discrimination parameter is calculated, based on whether the discrimination parameter is between energy ratios corresponding to the peaks of both the fitting functions.

14. The nuclear medicine diagnostic apparatus according to claim 13, wherein the parameter calculating device sets, when the discrimination parameter is determined improper, an upper limit or a lower limit of the energy ratio as the discrimination parameter.

15. The nuclear medicine diagnostic apparatus according to claim 10, further comprising a crystal display portion for displaying discrimination parameters and fitting functions of all blocks of a plurality of individual blocks formed by dividing the photon detecting elements; a selecting device for selecting an arbitrary block on the crystal display portion as a particular block; an adjustment display portion for displaying the fitting functions and the discrimination parameter of the particular block; a block display portion for displaying a composite function which is a sum of the fitting functions of all the blocks and the discrimination parameter of the particular block; and an adjusting device for adjusting the particular block and the discrimination parameter; wherein, when the discrimination parameter of the particular block is arbitrarily adjusted, the discrimination parameter adjusted is displayed on the adjustment display portion and the block display portion, to fine-adjust the discrimination parameter of the particular block.

* * * * *